United States Patent [19]

Fujita et al.

[11] 4,055,618

[45] Oct. 25, 1977

[54] PROCESS FOR PREPARING GRANULAR SORBIC ACID

[75] Inventors: Shigemi Fujita, Gifu; Masaru Goto, Hirakata, both of Japan

[73] Assignee: Nippon Gohsei Kagaku Kogyo Kabushiki Kaisha, Osaka, Japan

[21] Appl. No.: 723,484

[22] Filed: Sept. 15, 1976

[30] Foreign Application Priority Data

Sept. 23, 1975 Japan .............................. 50-115026
Nov. 21, 1975 Japan .............................. 50-140406

[51] Int. Cl.$^2$ ............................................. C07C 57/10
[52] U.S. Cl. .................. 264/141; 260/526 N; 264/143; 264/170; 264/330
[58] Field of Search ............... 264/143, 170, 141, 330, 264/176 F; 260/526 N; 425/67, 311, 378 S, 379 S

[56] References Cited

U.S. PATENT DOCUMENTS 3,758,563 9/1973 Vematsu et al. ................. 260/526 N

OTHER PUBLICATIONS

Feiser et al., Organic Chemistry, p. 169 (1956).

*Primary Examiner*—Robert F. White
*Assistant Examiner*—John A. Parrish
*Attorney, Agent, or Firm*—Armstrong, Nikaido & Marmelstein

[57] ABSTRACT

A process for preparing granular sorbic acid by adding water and/or a lower alkyl alcohol to powdery sorbic acid, kneading the resulting mixture under specific conditions to give a uniformly wetted powder, supplying the wetted powder to a screw type extruding machine, extruding the wetted powder through a perforated-cylinder die under specific conditions to give a vermicelli-like extrudate, and drying the extrudate. The obtained granules have sufficient rigidity and can be easily powdered by a mechanical action. When starch is added together with water and/or a lower alkyl alcohol, more rigid granules, but able to be easily powdered by a mechanical action such as agitation, are obtained.

2 Claims, No Drawings

PROCESS FOR PREPARING GRANULAR SORBIC ACID

BACKGROUND OF THE INVENTION

The present invention relates to a process for preparing granular sorbic acid.

Sorbic acid has excellent antifungal activity and nontoxicity, and has been effectively employed as a preservative for foods such as a fish-paste product, cheese or butter. However, when a powder of sorbic acid is employed in such a use, workability is not so good in comparison with granule. For instance, the fine power is easy to scatter in handling, and also troubles may occur upon wrapping or transportation.

For the purpose of solving such problems, it has been proposed to granulate the powdery sorbic acid. As a preferred granule, it is required to be so rigid that the granule is not broken away even under load or friction during transportation, and to be easily powdered by a mechanical action such as agitation or blending and to be uniformly dispersed into foods when the granule is added to foods, especially foods containing large amount of water upon blending, such as a fish-paste product, cheese or butter. Also, it is desirable that the granule is prepared in high yield.

It is proposed in Japanese patent publication No. 31091/1974 to granulate powdery sorbic acid by admixing sorbic acid with potassium sorbate. There is also proposed in Japanese patent disclosure No. 83324/1975 a process of granulating crystalline sorbic acid having a relatively large particle size. According to these knowm processes, granular sorbic acid having sufficient rigidity can be efficiently prepared, but the obtained granule is hard to be powdered by a mechanical action such as agitation or blending and cannot be uniformly dispersed into foods when it is added to foods such as a fish-paste product, cheese or butter and is blended. Therefore, there has been desired a process for preparing granular sorbic acid having more improved properties.

OBJECTS OF THE INVENTION

It is an object of the present invention to provide an improved process for preparing granular sorbic acid.

A further object of the invention is to provide a process for preparing granular sorbic acid having excellent phsyical properties by employing a conventional extruding machine.

A still further object of the invention is to provide granular sorbic acid which can be easily powdered by a mechanical action such as agitation or blending when it is added to foods and is blended.

These and other objects of the invention will become apparent from the description hereinafter.

DETAILED DESCRIPTION

It has now been found that the above-mentioned objects can be attained by adding water and/or a lower alkyl alcohol to powdery sorbic acid, kneading the resulting mixture to give a uniformly wetted powder, supplying the wetted powder to a conventional extruding machine, extruding the wetted powder through a perforated-cylinder die under specific conditions to give a vermicelli-like extrudate, and drying the extrudate.

In the process of the present invention, it is necessary to employ a fine powder of sorbic acid having a particle size of 30 to 150 $\mu$. When a coarse powder of more than 150 $\mu$ is employed, the obtained granule is hard to be powdered by a mechanical action when it is blended with a food. Also, when a very fine powder of less than 30 $\mu$ is employed, the handling becomes difficult in procedure of adding water and/or a lower alkyl alcohol to fine powder of sorbic acid. In general, sorbic acid is prepared by cleaving the polyester obtained by reacting crotonaldehyde with ketene, and the industrially prepared sorbic acid is usually in a form of a coarse powder. Therefore, it is necessary to mechanically pulverize a coarse powder of sorbic acid on the market to the particle size of 30 to 150 $\mu$. Although according to the present invention remarkable effects are obtained by limiting the particle size as stated above, it is preferable to employ powders having uniform particle shape in order to obtain granular sorbic acid having more improved properties. Powders having uniform particle shape may be prepared by optionally selecting steps of a process for preparing powdery sorbic acid. In order to provide fine powders having uniform particle shape, it is the most preferable to dissolve crystalline powders of sorbic acid in a hot water or lower alkyl alcohol to give a saturated solution and then to rapidly cool the solution by employing a condenser such as a vacuum evaporation condenser to precipitate crystal. A most part of the thus obtained powdery sorbic acid has a particle size within the range of 30 to 150 $\mu$. Very fine powders of less than 30 $\mu$ and coarse powders of more than 150 $\mu$ may be again dissolved in a hot water or lower alkyl alcohol and reprecipitated by rapidly cooling to give powdery sorbic acid having a particle size of the above range.

In the process of the present invention, water alone, a lower alkyl alcohol alone, or a mixture of water and the lower alkyl alcohol is first added to powdery sorbic acid. The amount of water is selected from the range of 8 to 35% by weight based on the total weight, and also the amount of the alcohol is selected from the range of 5 to 25% by weight based on the total weight. When the mixture of water and a lower alkyl alcohol is added to powdery sorbic acid, the critical limitations of the amount of the mixture employed vary depending on the mixing ratio of water and the alcohol. The amount of the mixture employed is from $(8m + 5n)/(m + n)$ to $(35m + 25n)/(m + n)\%$ by weight, wherein m is a mixing ratio by weight of water and n is a mixing ratio by weight of a lower alkyl alcohol, based on the total weight. In general, the less the amount of water or alcohol employed, the easier the drying. However, a small amount of water or alcohol below the above lower limit results in breakdown or choking of die. On the other hand, in case of a large amount of more than the above upper limit, the wetted powder has a tendency to stick during the kneading and extruding steps, and also the obtained granules are bulky and fragile. The employment of the lower alkyl alcohol makes drying easy and has the advantage of decreasing the blocking of the vermicelli-like extrudate. Further, when an alcohol solvent is used during preparing sorbic acid, the obtained powder containing the alcohol may be employed in the invention without completely removing the alcohol. In the present invention, lower alkyl alcohols having 1 to 3 carbon atoms are suitably employed. Examples of the lower alkyl alcohol are methanol, ethanol and isopropanol.

When it is desired to prepared granules having more sufficient rigidity and able to be easily powdered by a mechanical action, 0.2 to 3.5% by weight of starch based on the total weight may be further added as a binder to powdery sorbic acid. Starch may be added after gelatinizing it with water or hot water, or added in a form of powder. The amount less than 0.2% by weight cannot exhibit its effect. On the other hand, when the amount of starch is more than 3.5% by weight, the efficiency of blending it with sorbic acid lowers. In the present invention, any of starches can be employed. Examples of the starch are raw starches such as sweet potato starch, white potato starch, wheat starch, tapioca starch and corn starch, oxidized starch, dextrin, dialdehyde starch, and hydroxyethyl starch. When binders other than starch are employed, the obtained granules cannot be easily powdered by a mechanical action such as agitation or blending.

The thus obtained mixture is then sufficiently kneaded at a temperature of 10° to 45° C. for 10 minutes to 4 hours. As a kneading machine, any conventional kneader or a known high speed mixer such as Henschel type, gyratory-screw type or ribbon type mixer may be employed. The kneading step is essential for the present invention in order to get uniformly wetted powder, and it makes possible smooth extrusion, without bridging in a die, by a conventional extruding machine. Besides, the bulk density of the obtained granule is increased by sufficient kneading. When the kneading step is omitted in the present invention, fragile chips are extruded and troubles such as choking of die occur. Furthermore, the bulk density and rigidity of the so prepared granules are low, and the desired granules cannot be obtained. Upon carrying out the kneading, the temperature is selected from the range of 10° to 45° C. When the kneading is carried out at a temperature of more than 45° C., blocking occurs on walls of a kneading machine and the wetted powder is colored. Further, the kneading must be carried out at least for 10 minutes. However, even if the kneading is carried out for over 4 hours, the effects of kneading do not increase and, on the contrary, air is apt to be mixed, whereby the operation efficiency is lowered.

After the kneading step, the wetted powder is supplied to a conventional extruding machine. The conventional extruding machine in the present invention means a screw type extruding machine, in which only an extruding force is applied to the wetted powder and a lateral force at a die is not applied. As such a screw type extruding machine, a usual extruding granulator equipped with one or more screws and a die in the vicinity of the end of the screw may be employed. For instance, a screw type extruding machine disclosed in Japanese patent publication No. 18202/1965 may be employed. These conventional extruding machines have good workability due to their simple mechanism and give high yield of granule.

The use of a conventional extruding machine in the extruding step is one of the features of the present invention, and can be attained by the combination of the addition step of water and/or the alcohol and the kneading step. When the mixture without kneading it is subjected to the extruding by means of a conventional screw type extruding machine, satisfactory granules cannot be obtained due to troubles such as choking of die. In order to prepare satisfactory granules in such a case, it is necessary to provide the mixture to be extruded with not only extruding force by a screw but also lateral force by means of rolls or rotary blades which are located at an inner surface of die. But the application of such a lateral force lowers the production efficiency.

It is necessary to carry out the extruding under an extruding pressure at a die of 10 to 50 kg./cm.$^2$, and an extruding rate at a die of 1 to 4 g./cm.$^2$sec. When the pressure is less than 10 kg./cm.$^2$, the obtained granules have low bulk density and are fragile. Further, when the extruding rate is lower than 1 g./cm.$^2$sec., the choking of the die occurs, and when the extruding rate is higher than 4 g./cm.$^2$sec., there is a tendency that the extrudate sticks with each other.

The sorbic acid extruded through a perforated cylinder die in a form like vermicelli in length of 30 to 40 cm. is then dried on a wire net by contacting with a hot air. The extrudate is spontaneously cut into granules in length of not more than several millimeters in the drying step. At such a drying, the vermicelli-like extrudate spontaneously changes into granules without particularly passing through a cutting step, for instance, by merely vibrating the wire net. However, if desired, after drying the vermicelli-like extrudate may be subjected to cutting at a cutting step. The drying is carried out so as to reduce the content of volatile material to not more than 0.1% by weight. A fluidized bed drier equipped with a crusher on the bed may also be employed.

The granular sorbic acid obtained by the present invention is usually columnar grains in a diameter of 0.5 to 5 mm. in a length of 1 to 5 mm. and has a bulk density in a range of 0.4 to 0.5.

The present invention is more specifically described and explained by means of the following Examples.

EXAMPLE 1

A Nauta mixer, one of the gyratory-screw type mixers, was charged with 6.7 kg. of powdery sorbic acid containing less than 1% by weight of water and having a particle size of 30 to 150 $\mu$ and 3.3 kg. of water, and the kneading was carried out at a temperature of 20° C. for one hour. Then, the thus obtained mixture was supplied to a hopper of 7.5-horsepower single screw type extruding machine, and was extruded in a form like vermicelli through a die which had a thousand of round openings having a diameter of 1 mm. by means of a screw which rotated at a speed of 30 r.p.m. under an extruding pressure at a die of 30 kg./cm.$^2$ and an extruding rate at a die of 2.12 g./cm.$^2$sec. The amount of the mixture extruded was 60 kg. per hour. The thus extruded sorbic acid in a form like vermicelli was dropped onto a wire net which was gyrating, and was dried by blowing a hot air at a temperature of 90° C. from below the wire net. On the wire net, the extrudate was spontaneously cut into columnar grains having a length of 1 to 5 mm.

The bulk density and T value of the thus obtained granule were 0.42 and 99 %, respectively.

The T value is a value corresponding to the photo-transmission measured with a spectrophotometer at 430 m$\mu$ wave length through a cell of 1 cm. thickness containing a solution of 10 g. of the granular sorbic acid in 100 ml. of methanol, represented by percent, as compared with the photo-transmission through the same cell containing methanol.

A breaker was charged with 50 g. of the obtained granule and 50 ml. of water, and the mixture was agitated at a speed of 120 r.p.m. for 20 minutes. The granule broke down and the mixture changed to paste within 15 minutes.

EXAMPLE 2

A cake of sorbic acid containing 15% by weight of methanol was obtained from a methanolic solution of sorbic acid by means of a vacuum evaporation condenser. The particle size of the sorbic acid was 50 to 100 μ. A Nauta mixer was charged with the thus obtained cake, and the kneading was carried out at a temperature of 20° C. for 30 minutes. Then, the thus obtained mixture was supplied to a 25-horsepower single screw type extruding machine, and was extruded in a form like vermicelli through a die which had five thousands of round openings having a diameter of 1 mm. by means of a screw which rotated at a speed of 33 r.p.m. under an extruding pressure at a die of 30 kg./cm.$^2$, and an extruding rate at a die of 2.8 g./cm.$^2$sec. The amount of the mixture extruded was 400 kg. per hour. The thus extruded sorbic acid in a form like vermicelli was dropped into a through-flow dryer having a wire net of 60 meshes to pre-dry it, and was then dried in a fluidized bed dryer to reduce the volatile material content to not more than 0.1% by weight.

The thus obtained sorbic acid was columnar grains having a diameter of 1 mm. and a length of 2 to 5 mm. The bulk density and T value of the granule were 0.45 and 99%, respectively.

Comparative Example 1

The same procedure as in Example 1 was repeated except that the kneading time was cut down to 5 minutes. The choking of die occured, and the extruding capacity dropped. Also, the extruded sorbic acid was fragile, and a large amount of fine powder was produced and, therefore, the yield of the granule was low. The bulk density of the granule was 0.45.

Comparative Example 2

The same procedure as in Example 1 was repeated except that water was employed in an amount of 5 kg. (in an amount of about 75% by weight based on the weight of sorbic acid) instead of 3.3 kg. The amount of the mixture extruded was 150 kg. per hour. There was observed the blocking of the extrudate in the pre-drying apparatus. Also the obtained granules were very fragile.

Comparative Example 3

The same procedure as in Example 1 was repeated except that powdery sorbic acid having a particle size of 150 to 500 μ was employed instead of powdery sorbic acid having a particle size of 30 to 150 μ. The obtained granule was hard to be powdered by a mechanical action.

EXAMPLE 3

A saturated aqueous solution of sorbic acid was prepared by dissolving sorbic acid on the market in a hot water at 95° C., and was rapidly cooled by means of a vacuum evaporation condenser to give powdery sorbic acid having a particle size of 30 to 100 μ (water content: 30% by weight).

A Nauta mixer was charged with the thus obtained wet powder, and the kneading was carried out at a temperature of 25° C. for 15 minutes. Thereafter, the same procedure as in Example 1 was repeated to give granules.

The bulk density and T value of the granule were 0.45 and 99%, respectively.

A beaker was charged with 50 g. of the obtained granule and 50 ml. of water, and the mixture was agitated at a speed of 120 r.p.m. The granule broke down and the mixture changed to paste within 10 minutes. This shows that the granule obtained in this Example is superior to that obtained in Example 1.

EXAMPLE 4

The same procedure as in Example 1 was repeated except that 8 kg. of sorbic acid and 2 kg. of methanol were employed instead of 6.7 kg. of sorbic acid and 3.3 kg. of water and the kneading was carried out for 30 minutes instead of one hour.

The bulk density and T value of the obtained granule were 0.47 and 99%, respectively. The granule could be readily changed to pasted by agitating it in a wet state.

EXAMPLE 5

The same procedure as in Example 1 was repeated except that 3.4 kg. of sorbic acid, 34 g. of α-starch and 1.5 kg. of water were employed instead of 6.7 kg. of sorbic acid and 3.3 kg. of water.

The bulk density and T value of the obtained granule were 0.42 and 97.2%, respectively.

Also, the fragility and the dispersibility into water of the granule were 0.4% and 77.3%, respectively, which were measured as follows:

Fragility: Granules were screened by a 20-mesh sieve. Then a 200 ml. bottle was charged with 50 g. of the thus screened granules, and was placed in a shaker. Shaking was carried out for one hour at an amplitude of 40 to 50 mm. in the horizontal direction and at a rate of 200 to 220 times/minutes. Then the granules were screened for 30 minutes by a low tap type shaker to measure the particle distribution with employing 20-, 24- and 32-mesh sieves. The fragility was shown by a proportion in % by weight of particles having a particle size of not more than 24 meshes.

Dispersibility: This shows the easiness of crushing granule by a mechanical action such as agitation or blending. Granules were screened by a 20-mesh sieve. A 500 ml. separable flask was charged with 60 g. of a hot water at 50° C., and then 40 g. of the screened granules were added to the flask over 15 seconds with agitation at a rate of 400 r.p.m. After continuing the agitation for 10 minutes, the content was immediately screened in water by a 32-mesh sieve. Then the sorbic acid on the sieve was dried at a temperature of 60° C. by means of an air drier, and was weighed. The dispersibility was shown by a proportion in % by weight of particles having a particle size of not more than 32 meshes.

Further, the same procedure as the above was repeated except that the use of α-starch was omitted. The fragility and dispersibility of the obtained granule were 5.2% amd 58.9%, respectively.

EXAMPLE 6

The same procedure as in Example 2 was repeated except that 1% by weight of α-starch based on the total weight was further added to the cake of sorbic acid containing 15% by weight of methanol.

The obtained sorbic acid was columnar grains having a diameter of 1 mm. and a length of 2 to 5 mm. The bulk density and T value of the granule were 0.45 and 98.9%, respectively. Also, the fragility and dispersibility of the granule were 0.5% and 85%, respectively.

EXAMPLE 7

A saturated aqueous solution of sorbic acid was prepared by dissolving sorbic acid on the market in a hot water at 95° C., and was rapidly cooled by means of a vacuum evaporation condenser to give powdery sorbic acid having a particle size of 30 to 100 μ (water content: 20% by weight).

A Nauta mixer was charged with 2.5 kg. of the thus obtained wet powder and 20 g. of β-starch (which was gelatinized by employing 350 g. of a hot water), and the kneading was carried out at a temperature of 20° C. for 15 minutes. Thereafter, the same procedure as in Example 1 was repeated to give granules.

The bulk density and T value of the obtained granule were 0.42 and 99.0%, respectively. Also, the fragility and dispersibility of the granule were 0.2% and 82.5%, respectively.

What we claim is:

1. A process for preparing granular sorbic acid, which comprises the steps of
   a. adding at least one member selected from the group consisting of water and lower alkyl alcohols having 1 to 3 carbon atoms to powdery sorbic acid having a particle size of 30 to 150 μ, said water being employed in an amount of 8 to 35% by weight based on the total weight and said lower alkyl alcohol being employed in an amount of 5 to 25% by weight based on the total weight,
   b. kneading the resulting mixture at a temperature of 10° to 45° C. for 10 minutes to 4 hours to give a uniformly wetted powder,
   c. supplying the wetted powder to a hopper of a screw type extruding machine equipped with a perforated-cylinder die in the vicinity of an end of a screw, and extruding it under an extruding pressure at a die of 10 to 50 kg./cm.$^2$, and an extruding rate at a die of 1 to 4 g./cm.$^2$sec. to give a vermicelli-like extrudate, and
   d. drying the extrudate to give granules having a volatile material content of not more than 0.1% by weight.

2. The process of claim 1, wherein a starch is further added to said powdery sorbic acid in the step (a) in an amount of 0.2 to 3.5% by weight based on the total weight.

* * * * *